United States Patent [19]

Arala-Chaves

[11] 4,404,194

[45] Sep. 13, 1983

[54] IMMUNO-SUPPRESSIVE SUBSTANCE, ITS ISOLATION PROCESS, AND ITS THERAPEUTIC USE

[75] Inventor: Mario Arala-Chaves, Lisbon, Portugal

[73] Assignee: Berri-Balzac, Suresnes, France

[21] Appl. No.: 285,567

[22] Filed: Jul. 21, 1981

[30] Foreign Application Priority Data

Jul. 28, 1980 [FR] France ................................ 80 16582

[51] Int. Cl.³ .......................... C07G 7/00; A61K 37/00
[52] U.S. Cl. ................................ 424/177; 260/112 R; 435/68; 435/885
[58] Field of Search ..................... 260/112 R; 424/115, 424/177; 435/68, 885

[56] References Cited

U.S. PATENT DOCUMENTS 4,056,614 11/1977 Bonneau ............................. 424/105
4,117,118 9/1978 Harri .................................. 424/177
4,268,434 5/1981 Higerd ............................. 260/112 R

OTHER PUBLICATIONS

Arala-Chaves et al., J. Clin. Invest., vol. 64, pp. 871–883, 1979.

Primary Examiner—John C. Bleutge
Assistant Examiner—Patricia Short
Attorney, Agent, or Firm—Young & Thompson

[57] ABSTRACT

Figure 1:
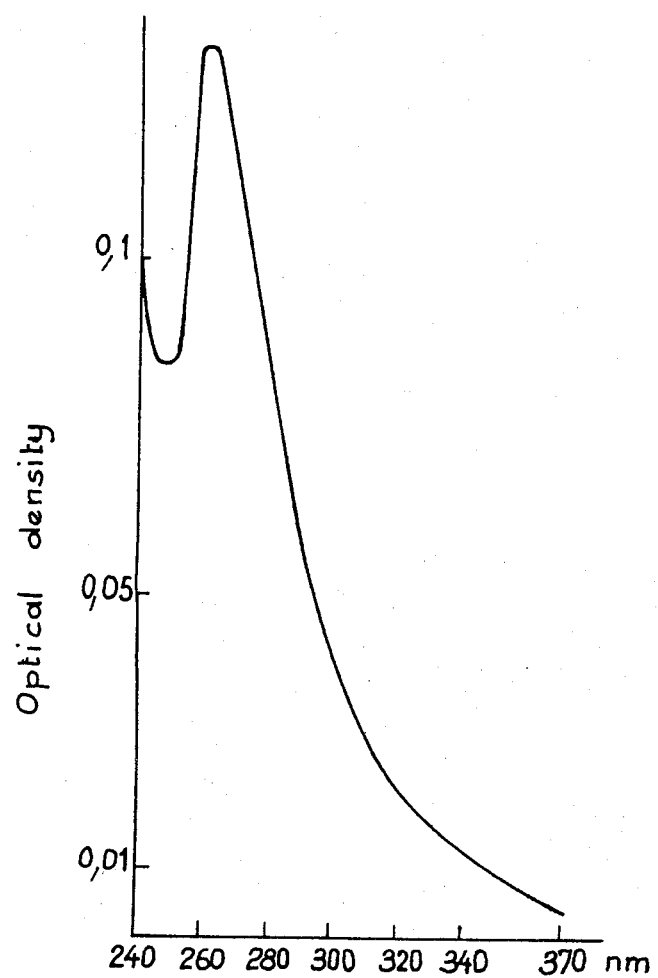

A protein with immuno-suppressive activity and with the following physico-chemical properties:
  isoelectric point: 4.25,
  ultraviolet absorption spectrum: as shown in FIG. 1, with a maximum at 260 nm,
  molecular mass: about 90,000 daltons,
  can be strained by Coomasie blue, but not by Methylene blue or PAS,
  desoxyribonuclease, ribonuclease A and neuraminidase proof, and degraded by $\alpha$, $\gamma$ and $\delta$ chymotrypsins and trypsine.

5 Claims, 3 Drawing Figures

IMMUNO-SUPPRESSIVE SUBSTANCE, ITS ISOLATION PROCESS, AND ITS THERAPEUTIC USE

DESCRIPTION

This invention is related to a new immuno-suppressive substance, its isolation process and its therapeutic use.

Mario P. ARALA-CHAVES et al. (J. Clin. Invest. vol. 64, Oct. 1979—p. 871-883) showed the crude extracts of *Streptococcus intermedius* had a strong immuno-suppressive activity.

The applicant has now succeeded in isolating the substance responsible for this immuno-suppressive activity, thus allowing its therapeutic use.

The new immuno-suppressive substance according to invention is a protein with the following physico-chemical properties:

1—its isoelectric point is 4.25,
2—it has an ultraviolet absorption spectrum, as shown in FIG. 1, with a maximum at 260 nm,
3—its molecular mass is about 90,000 daltons,
4—it can be stained by Coomasie blue; but neither by methylene blue nor PAS,
5—it is desoxyribonuclease, ribonuclease A and neuraminidase proof.

It is degraded by $\alpha$, $\gamma$ et $\delta$ chymotrypsins and trypsin.

Furthermore it is sensitive to heat; it is completely destroyed at 70° C. after 30 mn, partially destroyed at 56° C. after 30 mn and very slightly destroyed after incubation at 37° C. during 24 hours.

It also adheres to Sephadex and cellulose acetate and it is assumed that it contains phenylalanine as one of its main components.

It was also established that this substance can form complexes together with other biologically inactive components present in non-purified extracts.

The substance according to the invention can be obtained from products secreted by some microorganisms and especially by *Streptococcus Intermedius*.

The products secreted by these microorganisms can be obtained according to the technique previously described by Mario P. ARALA-CHAVES et al. (reference already mentioned) consisting in making a culture of the microorganism, separating it from the culture medium, on a dialysis membrane then washing the membrane, then removing by centrifugation the microorganisms from the washing liquid, then concentrating the liquid freed of microorganisms by ultracentrifugation or vacuum dialysis.

The separation of the substance according to this invention from these extracts can be performed as follows: these extracts are subjected to preparative isoelectrofocusing on a saccharose gradient at pH 3.5-6, the fractions with immunosuppressive activity are separated, these fractions are subjected to a preparative isoelectrofocusing on a saccharose gradient at pH 4-5, and the fraction with immunosuppressive activity is isolated.

The preparative isoelectrofocusing can be performed according to a technique based on the principles described by A. WINTER and C. KARISSON (1976) Preparative electrofocusing in density gradients. LKB Application Note 219, page 1-15.

The fractions containing the substance according to the invention, were isolated by measuring the immuno-suppressive activity according to the following techniques:

(a)-[$^3$H]-thymidine captation by human mononuclear cells stimulated by PHA (or PPD or MLC).

Blood mononuclear cells from 6 different donors are obtained from defibrinated blood after centrifugation on a Ficoll sodium metrizoate gradient according to the Boyum methodology (Scand. J. Clin. Lab. Invest. 21: 7-109).

The cells are cultured according to Du Bois et al. methodology (Tissue Antigens 3: 402-409) in Nunc Tubes. Minimal essential culture medium is used (MEM of Gibco Diagnostics), complemented with 20% fresh human AB serum inactivated by heating, and antibiotics (100 U/ml of penicillin, 100 g/ml of Streptomycin).

The medium is buffered by tris-HCl.

Phytohemagglutinin (PHA, Gibco) is used as a stimulant to a final concentration of 1/40.

Fractions to be tested are added either at the start of culture process or after stimulant addition.

Two days after the start of the culture process, 0.5 $\mu$Ci of [$^3$H]-thymidine is added to the cultures, 24 hours before collecting. Cultures are collected 24 hours later.

Immunosuppressive activity is measured by reduction of [$^3$H]-thymidine intake in these cultures in comparison with reference cultures stimulated by PHA.

(b) [$^3$H]-thymidine intake by human mononuclear cells stimulated by MLC.

This technique, a variant of the former, involves a mixed lymphocyte culture.

A mixed bidirectional lymphocyte culture is carried on with $1.5$-$10^5$ mononuclear cells from to HLA-incompatible human donors.

Fractions to be tested are added at the start of culturing at 1/200 to 1/25 600 dilutions.

Five days after the start of the culture, 0.5 $\mu$Ci of [$^3$H]-thymidine are added to the culture. Cultures are collected 24 hours later.

(c) Immunization of human mononuclear cells against sheep red blood cells (SRBC), consisting in inhibiting the in vitro generation of mononuclear cells of human peripheric blood capable of producing antibodies against sheep red cells.

The methodology described by Mario P. ARALA-CHAVES et al. was used (reference already mentioned).

(d) In vivo testing in mice.

The method previously described by Mario P. ARALA-CHAVES et al. was used (reference already mentioned).

The isolation of substance from *Streptococcus Intermedius* according to the invention will be explained hereafter.

*Streptococcus intermedius* is cultured under anaerobic conditions on 100 mm in diamater dialysis membrane disks (letting substances with molecular mass up to 12,000-14,000 go through) lying on a tryptone-glucose-agar culture medium (containing 20 g tryptone, 5 g glucose, 4 g $K_2HPO_4$, 1 g $KH_2PO_4$, 2 g NaCl, 250 mg $MgSO_4.7H_2O$, 17 mg $MnSO_4$ and 15 g agar in one distilled water liter).

0.1 ml of bacterial suspension containing $10^8$ cells per ml is spread on the dialysis membrane with the help of a cotton wool wad.

The culture is carried on during 24 hours at 37° C. Then the membranes are taken out and left with a minimal 0.05 M, pH 7.5 volume. The washing liquid is then centrifuged at 29,000 g during 15 mn to separate the microorganisms. The supernatant is concentrated about 10 times by ultra centrifugation under positive pressure with a PM 10 Amicon filter.

This last operation moreover allows the separation of dialyzable nutriments coming from culture medium. Concentrated preparations containing 1,490 μg/ml protein are obtained.

Concentrated preparations of products secreted by Streptococcus Intermedius are them put through a double preparative isoelectrofocusing.

This preparative isoelectrofocusing is done on a 110 ml LKB 8 100-1 column. First a 3.5 to 6 pH gradient is used mixing equal proportions of 3.5–5 pH (LKB 1 809-111) and 4–5 pH (LKB 4-6) ampholytes in order to obtain a final ampholytes concentration of 2% (weight/volume).

A second preparative isoelectrofocusing consists of a 4–5 pH gradient in order to separate the fractions semi-purified by the first isoelectrofocusing. For this purpose pH 4–5 ampholytes (Servalyst) are used, with a final ampholytes concentration of 2% (weight/volume).

The anode solution, at the bottom consists in 1.0 M phosphoric acid and the cathode solution, at the top consists in 1.0 M sodium hydroxide. In addition the pH gradient is stabilized in order to prevent convection with the help of a saccharose vertical density gradient made by mixing a dense saccharose solution (50% p/v) with a light saccharose solution (5% p/v) using a LKB 8 121 gradient mixer.

Practically, the column is filled up to ⅔ of its volume and the samples are mixed with the dense solution in a proportion of 2/1 (v/v) and laid carefully on the top of the gradient. Afterwards the rest of the gradient solution is laid on top. The samples are made in each case of 3 different concentrated preparations of products secreted by Streptococcus Intermedius or of 2 preparations of semi-purified fractions of these concentrated preparations.

All the samples are remade in a 3 to 6 ml volume after a whole night's dialysis at 4° C. against 1% w/v glycine.

The isoelectrofocusing conditions consist in a 1,600 volts constant tension during 16 hours with a 10 mA initial intensity and a final intensity of 2 mA. Afterwards, the voltage is increased up to 1,800 volts for four more hours. During the experiment, the column is cooled, the temperature being 2° C. at the entry and 5° at the outlet of the column.

The column elution is effectd by pushing the gradient from the bottom up to the top with the distilled water injection with help of a peristaltic pump, the flow being approximately 25 ml per hour. The eluate is collected in 1.5 ml fractions. The pH is measured in each tube at ambient temperature.

The fractions are pooled according to their optical densities measured at 280 nm.

Ampholytes and saccharose are removed from the fractions by dialysis against a large volume of a 1% glycine solution, then by at least two stages of vacuum dialysis. When the greater part of the liquid is extracted from the dialysis bag, the residual solution is mixed with 50 volumes of MEM medium (Gibco Diagnostics) and samples are dialyzed again in order to bring back to the same volume as the initial sample which was fractionated.

Figure 2:
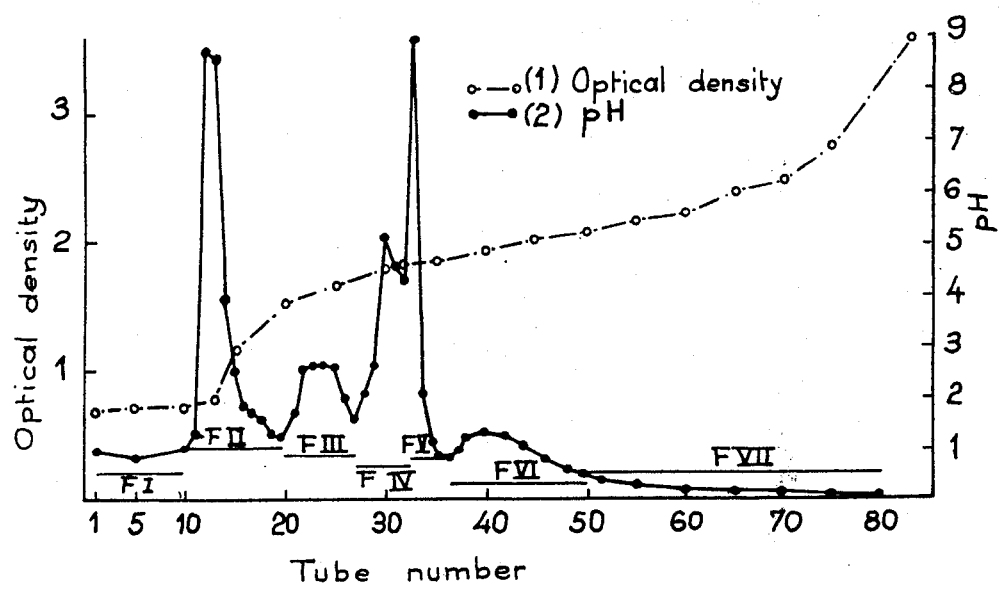

At the end of the first division, the fractions were put together in 7 main fractions (FI to F VIII) according to their optical densities. In FIG. 2 is showed the optical densities of the fractions and the 7 main fractions put together. The pH of the eluted fraction is also shown in FIG. 2.

The immunosuppressive activity was found in fractions FV (pH 4.52–4.68) and FVI (pH 4.70–5.25) but mainly in fraction FVI, by in vitro tests of [$^3$H]-thymidine intake inhibition by culture stimulated by PHA or MLC and in vivo tests in mice.

The combined fractions FV+VI account for 6% of the total content in proteins of the initial concentrated preparation.

Figure 3:
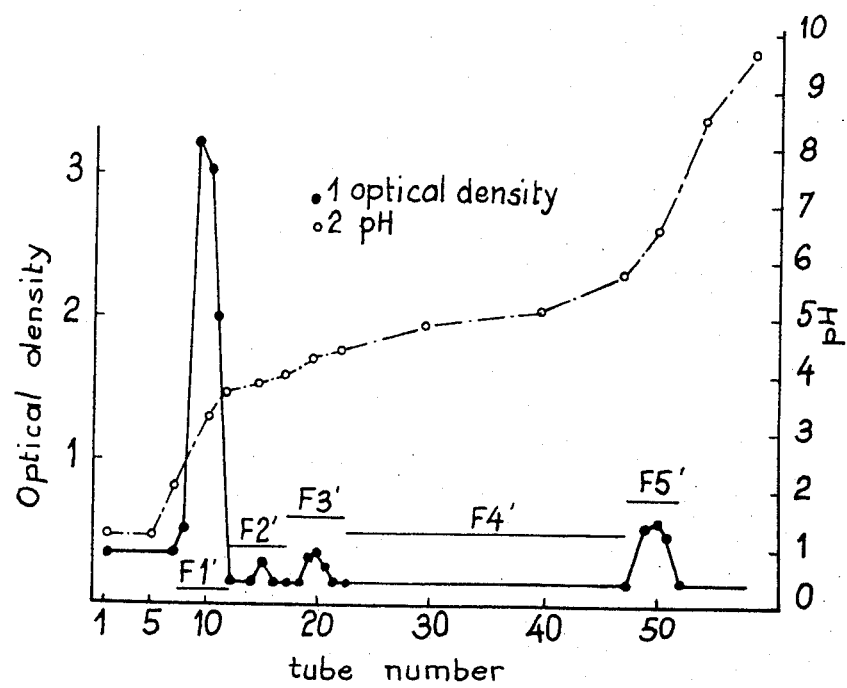

The combined fractions FV+VI were subjected to a second division by isoelectrofocusing between pH 4 and 5. Fractions optical densities obtained thus and their pH are shown in FIG. 3.

Immunosuppressive activity was found in F'3 fraction (pH 4.1–4.4). This fraction contains 15 μg/ml protein. That means about 1% of initial concentration in proteins. The immunosuppressive activity was observed in the four above mentioned four tests (a, b, c, and d).

In Table I hereafter, are given the results obtained in [$^3$]-thymidine uptake tests of cultures stimulated by PHA and MLC.

TABLE I

| Concentration | [$^3$H]-THYMIDINE | |
|---|---|---|
| | PHA | MLC |
| 0 (reference) | 35.821 ± 1.889 | 33.571 ± 1.169 |
| 1/400 | 56 ± 11 (0,15%) | 64 ± 19 (0,19%) |
| 1/800 | 75 ± 7 (0,21%) | 134 ± 11 (0,4%) |
| 1/1600 | 107 ± 15 (0,3%) | 171 ± 15 (0,5%) |
| 1/3200 | 1.074 ± 111 (3%) | 235 ± 11 (0,7%) |
| 1/6400 | 9.393 ± 396 (26%) | 2.014 ± 181 (6%) |

The numbers in brackets indicate the mean values of the three tests, given in percentage compared with references.

In Table II hereafter are given the results obtained in human mononuclear cell immunization tests against SRBC.

TABLE II

| Concentration | % compared with reference |
|---|---|
| 2 U MLC | 50 |
| 4 | 25 |
| 8 | 3 |

For the in vivo test in mice, a F'3 fraction quantity was injected (corresponding to 1 μg protein) in mice by intraperitoneal route, two days before antigen induced by sheep red blood cells. An answer was obtained which was 5±1.5% of the one obtained in reference mice without protein injection.

The F'3 fraction was put through an analytic electrofocusing on a polyacrylamide gel between 4–6-pH. Only one band is obtained colorable by Coomasie blue. This band has a 4.25 isoelectric point. This band is not colorable either by methylene blue or by PAS (glycoproteins detection method using periodic acid and Schiff's reagent).

The UV absorption spectrum between 240 and 370 nm represented in FIG. 1, reveals a maximum of absorption at 260 nm. The molecular mass of the substance present in the F'3 fraction was estimated at 90,000 daltons, by measuring the migration on 7.5% polyacrylamide gels according to the Weber and Osborn method (J. Biol. Chem. 244, 4406-4412) and by measuring the mobility according to the Thorun and Maurer method (Disc electrophoresis and related techniques of polyacrylamide gel electrophoresis—Maurer, Walter de Gruyter Berlin Eds. 8-31).

The substance present in the F'3 fraction is sensitive to proteolytic activity of α, δ and γ chymotrypsins and of trypsin. It is resistant to desoxyribonuclease, ribonuclease A and neuraminidase. On the other hand, it is very sensitive to heat: it is totally destroyed at 70° C. after 30 mn, partially destroyed at 56° C. after 30 mn and very slightly destroyed at 37° C. during 24 hours.

These characteristics confirm the proteinic nature of the isolated substance.

It was moreover established that this protein adheres to Sephadex and to cellulose acetate. Thus, considering its absorption maximum, it is supposed to contain phenylalamine as one of its main constituents.

It appears that the isolated protein has a noteworthy immunosuppressive activity that is seen in the different tests performed at very low doses, much lower than LD 50 by IP route in mice, which is higher than 1 mg/kg.

The substance according to the invention can be isolated from products secreted by the following microoganisms or organisms:

a-Bacteria

Filamentous Gram+ Bacteria

Actinomyces (*A. israeli, A. viscosus, A. naeslundii, A. odontolyticus*)
Corynebacteries dont *C. diphteriae, C. pyogenes, C. pseudotuberculosis, C.* (Propionibacterium) *acnes, G. Granulosum, C. parvum, C. vaginale.*
  Listeria dont *L. monocytogenes.*
  *Erysipelothrix rhusiopathiae.*
  Bacillus dont *B. cereus.*
  Lactobacillus dont *L. casei.*
  Clostridies dont *C. perfringens.*

Acido alcohol resistant Bacteria

Mycobacteria *M. Tuberculosis, M. bovis, M. avium, M. leprae.*

Cocci Gram+

Staphylococus *S. aureus, S. epidermididis.* Streptococus: *S. pyogenes, S. mutans, S. mitis, S. sanguis, S. salivarius, S. intermedius* et *S.* (Diplococcus) *pneumoniae.*
Micrococcus sp et *Diplococcus* sp *anaerobic.*

Filamentous Gram-Bacteria

*Leptotrichia buccalis*
Fusobacterium (*F. fusiforme, F. nucleatum*)
Bacteroides (*B. melaninogenicus* ssp. *intermedius* et *melaninogenicus, B. oralis, B. asaccharolyticus*).
*Bacillus* (Capnocytophaga) *ochraceus.*
*Campylobacter* (Vibrio) *fetus, C. coli, C. jejuni, C. sputorum.*
Spirillum
*Eikenella corrodens*
*Ramibacterium ramosum*

Cocci Gram-

Neisseria (*N. gonorrhoeae, N. meningitidis, N. mucosa, N. perflava, N. subflava*)
*Veillonella parvula*
*Ristella fragilis*

Enterobacteria: Enterobacter, Serratia, Klebsiella, Citrobacter, Escherichia (*E. coli*), Proteus, Providencia.
Pseudomonas dont *P. aeruginosa*
*Francisella tularensis*
Versinia (*Y. pestis, Y. pseudotuberculosis, Y. enterocolitica*)
Haemophilus (*H. influenzae, H. aegyptius, H. ducreyi*)
Brucella (*B. melitensis, B. abortus, B. suis*)
Aeromonas
Moraxella
Bordetella (*B. pertussis, B. bronchiseptica*)
Pasteurella (*P. multocida, P. pneumotropica*)
Vibrio (*V. cholerae, V. eltor*)

Spirochetes

Leptospira (*L. icterahaemorrhagiae*)
Treponema (*P. pallidum*)
Borrelia (*B. recurrentis*)

Mycoplasma

Mycoplasma (*M. orale, M. salivarium*)

Rickettsia

Rickettsia (*R. mooseri, R. prowazeki*)
Coxiella (*C. burneti*)

Cae

Chlamydia (*C. trachomatis, C. lymphogralumatosis*) (*C. psittaci*)

b-Fungi

Candida (*C. albicans*)
*Cryptococcus neoformans*
*Histoplasma caspulatum*
*Aspergillus fumigatus* c-Parasites

Protozoa

Amibes: Entamoeba (*H. histolytica*)
Flagellata
  -flagelles sanguicoles et S.R.E.
  Trypanosoma (*T. gambiense, T. cruzi*)
  Leischania (*L. donovani, L. tropica*)
  -flagelles intestinaux et genito-urinaires
  *Trichomonas vaginalis*
  *Giardia intestinalis*

Sporozoa

*Toxoplasma gondii*
Plasmodium (*P. falciparum, P. vivax*)
*Pneumocystis carinii*

Helminths

-Nematodes
*Ascaris lumbricoides*
*Strongyloides stercoralis*
*Trichinella spiralis*
*Onchocerca volvulus*
-Flate-worms
  *Fasciola hepatica*
  Shistosoma (*S. mansoni*)
-Tape-worms
  *Taenia solium*
  *Echinococcus granulosus.*

The substance according to the invention can be used in therapeutics as an immunosuppressor.

For this purpose, the substance according to the invention can be presented under different galenic forms such as solution or suspension in an physiological saline solution or in an oil excipient or water in oil or oil in water emulsion for intradermic sub-cutaneous, intramuscular, intravenous, intrarachidian administration or in lipidic particle integrated form, in lyophilized form, spray form, drinking form, as tablets, coated tablets or capsule for per os administration or also in suppositories for rectal administration or ovules for gynaecologic administration.

It can also be presented as an ointment, a spray, or a gel in an appropriate excipient for a topical administration.

It can be administered to human at a dosage of 0.1 to 10 mg.

I claim:

1. Protein obtained from the products secreted by microorganisms, having immuno-suppressive activity and the following physico-chemical properties:
   (1) isoelectric point: 4.25,
   (2) ultraviolet absorption spectrum: as shown in FIG. 1, with a maximum at 260 nm,
   (3) molecular mass: about 90,000 daltons as estimated by measuring the migration on a polyacrylamide gel,
   (4) can be stained by Coomasie blue but not by Methylene blue or PAS,
   (5) desoxyribonuclease, ribonuclease A and neuraminidase proof and degradable by $\alpha$, $\gamma$ and $\delta$ chymotrypsins and trypsin.

2. Process for the production of a protein according to claim 1, comprising subjecting the products secreted by microorganisms whose extracts have immuno-suppressive activity, to a preparative isoelectrofocusing on a saccharose gradient at pH 3.5–6, separating the fractions with immuno-suppressive activity, subjecting these fractions to a preparative isoelectrofocusing on a saccharose gradient at pH 4–5 and isolating the fraction with immuno-suppressive activity.

3. Process according to claim 2, in which said microorganisms are *Streptococcus Intermedius*.

4. Therapeutic composition having immuno-suppressive activity comprising a protein as claimed in claim 1 in admixture with a therapeutically acceptable excipient.

5. A composition according to claim 4, in unit dosage form, in which said protein is present in the amount of 0.1 to 10 mg.

* * * * *